US00PP25265P3

(12) United States Plant Patent
Tsukahara

(10) Patent No.: US PP25,265 P3
(45) Date of Patent: Jan. 27, 2015

(54) ***PETUNIA* PLANT NAMED 'PBLRS38-0'**

(50) Latin Name: ***Petunia* hybrid**
Varietal Denomination: PBLRS38-0

(71) Applicant: Jun Tsukahara, Fukuoka (JP)

(72) Inventor: Jun Tsukahara, Fukuoka (JP)

(73) Assignee: Suntory Flowers Ltd (JP)

( * ) Notice: Subject to any disclaimer, the term of this patent is extended or adjusted under 35 U.S.C. 154(b) by 214 days.

(21) Appl. No.: 13/815,142

(22) Filed: Jan. 31, 2013

(65) Prior Publication Data

US 2014/0215669 P1 Jul. 31, 2014

(51) Int. Cl.
*A01H 5/00* (2006.01)

(52) U.S. Cl.
USPC ..... Plt./356.13

(58) Field of Classification Search
USPC ..... Plt./356.13, 356.1
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'PBLRS38-0' is disclosed, characterized by unique bicolored flowers, a compact growth habit, and vigorous, easy to grow plants. The new variety is a *Petunia,* suitable as an outdoor garden or container plant.

2 Drawing Sheets

Figure 1:
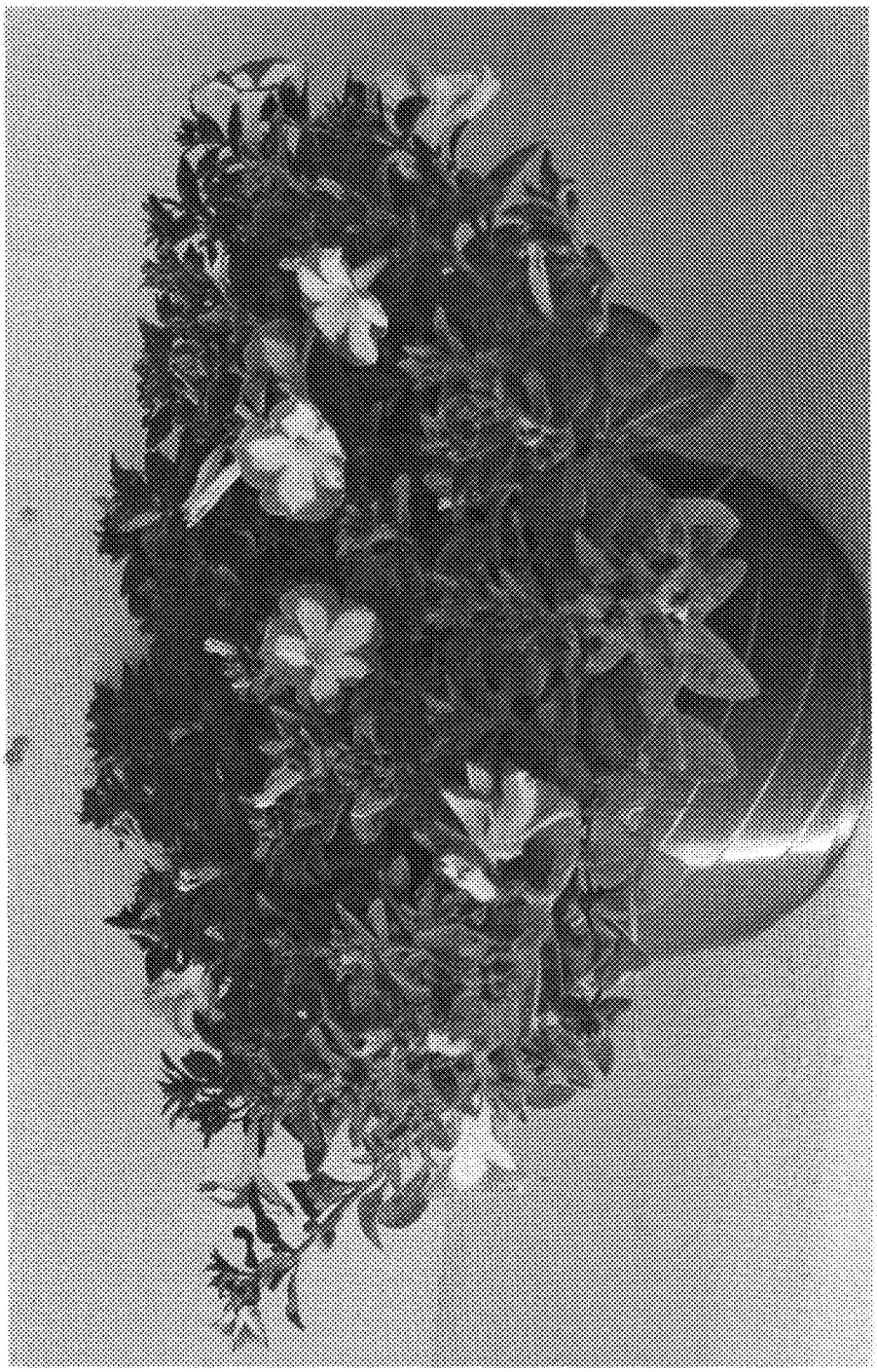

Latin name of the genus and species: *Petunia* hybrid.
Variety denomination: 'PBLRS38-0'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September of 2008. The new variety was discovered in May of 2009 by the inventor in a group of seedlings resulting from that crossing, in a research greenhouse in Yame, Fukuoka, Japan.

Asexual reproduction of the new cultivar 'PBLRS38-0' by vegetative cuttings was first performed at a research greenhouse in Yame, Fukuoka, Japan in May of 2009. Subsequently one generation has been produced and has shown that the unique features of this cultivar are stable and reproduced true to type.

SUMMARY OF THE INVENTION

The cultivar 'PBLRS38-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'PBLRS38-0.' These characteristics in combination distinguish 'PBLRS38-0' as a new and distinct *Petunia* cultivar:

1. Bicolor flower with a center white colored star pattern and a vibrant red-purple outer margin.
2. Vigorous, easy to grow plants.
3. Very compact growth habit

COMPARISON TO THE PARENT VARIETIES

Plants of the new cultivar 'PBLRS38-0' are similar in most horticultural characteristics to plants of the unnamed proprietary seed parent. However, the new cultivar produces a wider leaf and a creeping growth habit compared to the seed parent's medium growth habit. Additionally, plants of the seed parent produce wine red with white colored flowers, whereas 'PBLRS38-0' produces Bright red-purple with white colored flowers.

Plants of the new cultivar 'PBLRS38-0' are similar in most horticultural characteristics to plants of the unnamed proprietary pollen parent. However, the pollen parent produces thicker leaves, and a smaller overall flower size than found on plants of the new cultivar. Additionally, the pollen parent produces shorter peduncles than those of the new cultivar.

COMPARISON TO COMMERCIAL VARIETIES

The new cultivar can be compared to the patented commercial variety 'Daiichi Bluette Purple2' U.S. Plant Pat. No. 22,236. 'PBLRS38-0' is similar to this commercial variety in most horticultural characteristics, most specifically, in plant habit, however, plants of the new cultivar produce bicolor flowers, compared to 'Daiichi Bluette Purple2' producing single color flowers.

The new cultivar can be compared to the patented commercial variety 'Bluette Gradation Pink' U.S. Plant Pat. No. 22,237. 'PBLRS38-0' is similar to this commercial variety in most horticultural characteristics, however, plants of the new are more compact than this comparator. Additionally while both varieties produce bi color flowers, the new cultivar produces a more definite star pattern in the center of the flower, and has a deeper and brighter red-purple outer coloration to the flower.

BRIEF DESCRIPTION OF THE PHOTOGRAPH

The accompanying photograph in FIG. 1 illustrates in full color typical flowers and foliage of 'PBLRS38-0'.

Figure 2:
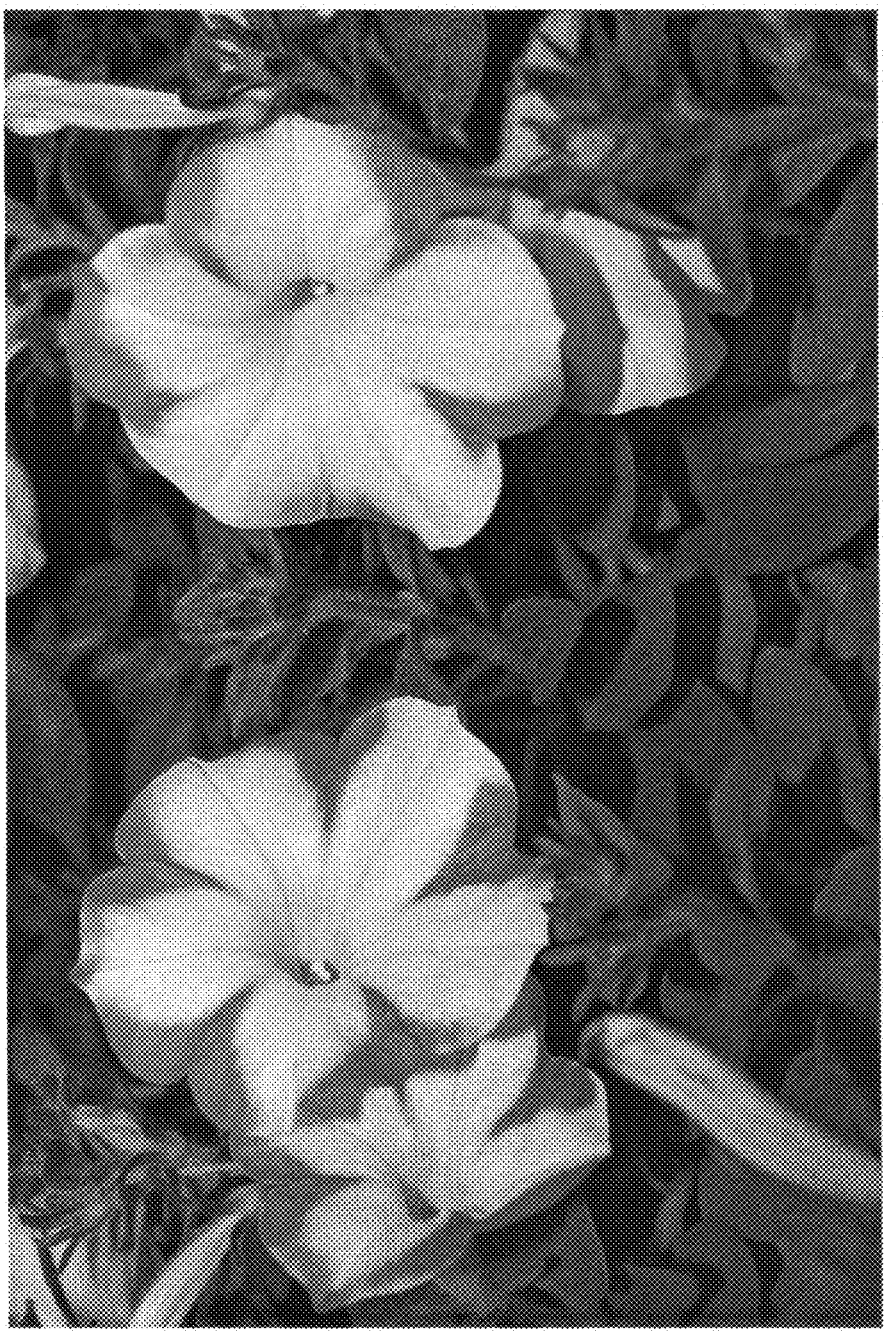

FIG. 2 illustrates a typical plant of 'PBLRS38-0' grown in a greenhouse, in a 10 inch commercial basket. Age of the plant photographed is approximately 20 weeks from 5 rooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'PBLRS38-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.
Botanical classification: *Petunia* hybrid 'PBLRS38-0'.

PROPAGATION

Time to initiate roots: About 7 days at approximately 25° C.
Time to develop roots: About 14 to 21 days at approximately 25° C.
Root description: Fine, fibrous.

PLANT

Growth habit: Mounding to semi trailing.
Age of the plant described: Approximately 20 weeks from 5 rooted cuttings.
Pot size of plant described: 10 inch basket.
Height: Approximately 15 cm from soil line to top of plant.
Plant spread: Approximately 50 cm at widest point.
Growth rate: Rapid.
Branching characteristics: Free branching.
Length of primary lateral branches: Approximately 15 cm.
Quantity of primary lateral branches: Approximately 70.
Characteristics of primary lateral branches:
- *Diameter.*—Approximately 0.3 cm.
- *Color.*—Near RHS Green 141C.
- *Texture.*—Highly pubescent.
- *Strength.*—Highly flexible, moderately strong.

Internode length: Average 2.2 cm.

FOLIAGE

Leaf:
- *Arrangement.*—Opposite.
- *Quantity.*—Approximately 12 per main lateral branch.
- *Average length.*—Approximately 3.9 cm.
- *Average width.*—Approximately 2.0 cm.
- *Shape of blade.*—Obovate.
- *Apex.*—Acute.
- *Base.*—Obtuse.
- *Margin.*—Entire.
- *Appearance of top surface.*—Matte.
- *Appearance of top surface.*—Matte.
- *Pubescence.*—Very short, less than 1 mm hairs, densely covering top and bottom leaf surfaces.
- *Aspect.*—Very slightly upwardly curved.
- *Color.*—Young foliage upper side: Near RHS Green 138A. Young foliage under side: Near RHS Green 138B. Mature foliage upper side: Near RHS Green 137A. Mature foliage under side: Near RHS Green 138A.
- *Venation.*—Type: Pinnate. Venation color upper side: Near RHS Yellow-Green 144C. Venation color under side: Near RHS Yellow-Green 144C.
- *Petiole.*—Length: Approximately 0.4 cm. Diameter: Approximately 0.2 cm. Color: Near RHS Yellow-Green 144C. Texture: Pubescent.

FLOWER

Natural flowering season: Spring and Summer.
Days to flowering from rooted cutting: Approximately 50.
Inflorescence and flower type and habit: Single salverform with fused petals.
Rate of flower opening: Approximately 2 to 3 days from bud to fully opened flower.
Flower longevity on plant: Approximately 1 week.
Approximate quantity of flowers per plant: Approximately 100 flowers and buds.
Flowers self cleaning:
Bud:
- *Shape.*—Oblong.
- *Length.*—Approximately 4.0 cm.
- *Diameter.*—Approximately 1.0 cm.
- *Color.*—Near RHS Yellow-Green 145D, distal end near Purple 77A.

Flower size:
- *Diameter, widest point.*—Approximately 5.2 cm.
- *Overall length.*—Approximately 4.5.
- *Flower tube length.*—Approximately 2.8 cm.
- *Flower tube diameter at distal end.*—Approximately 1.0 cm.
- *Flower tube diameter at proximal end.*—Approximately 0.5 cm.

Petals:
- *Length from throat.*—About 2.5 cm.
- *Width.*—About 3.0 cm.
- *Quantity.*—5, fused.
- *Texture.*—Smooth.
- *Apex.*—Mucronate.
- *Margin.*—Entire.

Color:
- *When opening.*—Inner surface: Near RHS Green-white 157B, with thick, blotchy margin near Red-Purple 72B and Red-Purple N74A, both colors present. Outer surface: Near RHS Yellow-Green 145D with thick, blotchy margin near Red-Purple N74C.
- *Fully opened.*—Inner surface: Near RHS White N155D, with thick, blotchy margin near Red-Purple N74B. Outer surface: Near White N155D, with thick, blotchy margin near Red-Purple N74C. Vein coloration near Yellow-Green 145C. Flower throat (inside): Near White N155D, vein coloration near Yellow-Green 145B. Flower tube (outside): Near White N155D, vein coloration near Yellow-Green 145B. Petal color, fading to: Near RHS White N155D, with thick, blotchy margin near Violet 83D.

Calyx/sepals:
- *Quantity per flower.*—5.
- *Shape.*—Oblong.
- *Length.*—Approximately 1.7 cm.

*Width.*—Approximately 0.4 cm.
*Apex.*—Acute.
*Base.*—Truncate.
*Margin.*—Entire.
*Texture.*—Pubescent, all surfaces.
*Color.*—Upper Surface: Near RHS Green 137B. Lower Surface: Near RHS Green 137C.

Peduncle:
*Length.*—Approximately 2.3 cm.
*Diameter.*—Approximately 0.2 cm.
*Color.*—Near RHS Green 138A.
*Orientation.*—Approximately 45 degree angle from stem.

Fragrance: Sweet.

REPRODUCTIVE ORGANS

Stamens:
*Number.*—5.
*Filament length.*—Approximately 1.4 to 2.1 cm.

Anthers:
*Length.*—Approximately 0.1 cm.
*Shape.*—Globular.
*Color.*—RHS White N155B.
*Pollen.*—Moderate, colored near White N155B.

Pistil:
*Number.*—1.
*Length.*—Approximately 1.7 cm.
*Style.*—Length: Approximately 1.6 cm. Color: Near RHS Green-White 157C.
*Stigma.*—Shape: Oblate. Color: Near RHS Green143C. Ovary Color: Near RHS Green143C.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° C. to 35° C.

What is claimed is:

1. A new and distinct cultivar of *Petunia* plant named 'PBLRS38-0' as herein illustrated and described.

* * * * *